(12) United States Patent
Upah et al.

(10) Patent No.: US 11,298,357 B2
(45) Date of Patent: Apr. 12, 2022

(54) BOVINE SUPPLEMENT FOR NEONATAL CALVES

(71) Applicant: TECHMIX, LLC, Stewart, MN (US)

(72) Inventors: Nathan C. Upah, Clutier, IA (US); Aaron N. Fritchen, Des Moines, IA (US); Dennis M. McKilligan, Ames, IA (US); Bradley W. Kolstad, Waconia, MN (US)

(73) Assignee: TechMix, LLC, Stewart, MN (US)

(*) Notice: Subject to any disclaimer, the term of this patent is extended or adjusted under 35 U.S.C. 154(b) by 0 days.

(21) Appl. No.: 16/117,227

(22) Filed: Aug. 30, 2018

(65) Prior Publication Data

US 2020/0069692 A1 Mar. 5, 2020

(51) Int. Cl.

| | |
|---|---|
| *A61K 31/522* | (2006.01) |
| *A61K 9/00* | (2006.01) |
| *A61K 36/82* | (2006.01) |
| *A61K 47/44* | (2017.01) |
| *A23K 10/30* | (2016.01) |
| *A61K 47/12* | (2006.01) |
| *A23K 50/10* | (2016.01) |
| *A23K 50/60* | (2016.01) |
| *A23K 20/22* | (2016.01) |
| *A61K 47/36* | (2006.01) |

(52) U.S. Cl.
CPC ............ *A61K 31/522* (2013.01); *A23K 10/30* (2016.05); *A23K 20/22* (2016.05); *A23K 50/10* (2016.05); *A23K 50/60* (2016.05); *A61K 9/006* (2013.01); *A61K 36/82* (2013.01); *A61K 47/12* (2013.01); *A61K 47/36* (2013.01); *A61K 47/44* (2013.01)

(58) Field of Classification Search
CPC ........ A23K 50/60; A23K 10/30; A23K 50/10; A61K 36/82; A23L 29/269; A23L 29/30; A23L 33/125
See application file for complete search history.

(56) References Cited

U.S. PATENT DOCUMENTS

| | | |
|---|---|---|
| 5,223,294 A | 6/1993 | Takenawa |
| 5,624,698 A * | 4/1997 | Dake .................. A23L 2/38 426/330.3 |
| 2002/0035096 A1 | 3/2002 | Lawter et al. |
| 2007/0298142 A1 | 12/2007 | Godbee et al. |
| 2008/0038409 A1* | 2/2008 | Nair .................. A23G 1/56 426/73 |
| 2011/0123651 A1 | 5/2011 | Mower et al. |
| 2017/0231996 A1* | 8/2017 | Levi .................. A61K 47/10 514/263.31 |
| 2017/0354175 A1* | 12/2017 | Karanewsky ......... A23L 27/205 |

FOREIGN PATENT DOCUMENTS

WO    WO-2018058039 A1 *  3/2018  ............. A23K 10/00

OTHER PUBLICATIONS

Clif Shot Turbo Double Espresso EnergyGel (accessed via https://www.clifbar.com/products/clif/shot-energy-gel/double-expresso on May 21, 2020).*

Notification of Transmittal of the International Search Report and the Written Opinion of the International Searching Authority, the Search Report and Written Opinion, dated Apr. 15, 2019.

Rebello, Candida J., et al., "The Role of Meal Viscosity and Oat B-Glucan Characteristics in Human Appetite Control: a Randomized Crossover Trial," Nutrition Journal, vol. 13, No. 49 (2014), BioMed Central.

\* cited by examiner

*Primary Examiner* — Melissa L Fisher
(74) *Attorney, Agent, or Firm* — DeWitt LLP

(57) ABSTRACT

The present invention relates generally to a feed supplement preparation for administration to ruminant animals and, more particularly, to a formulation for an oral bovine supplement for neonatal calves that delivers naturally occurring caffeine, antioxidants and other electrolytes in a stable liquid form of moderate viscosity.

14 Claims, No Drawings

BOVINE SUPPLEMENT FOR NEONATAL CALVES

CROSS-REFERENCED TO RELATED APPLICATIONS

Not applicable

STATEMENT REGARDING FEDERALLY SPONSORED RESEARCH OR DEVELOPMENT

Not applicable

BACKGROUND OF THE INVENTION

I. Field of the Invention

The present invention relates generally to a feed supplement preparation for administration to ruminant animals and, more particularly, to a formulation for an oral bovine supplement for neonatal calves that delivers naturally occurring caffeine, antioxidants and other electrolytes in a stable liquid form of moderate viscosity.

II. Related Art

It is known to administer several essential nutrients to neonatal calves following parturition, in addition to colostrum. Reducing calf mortality resulting from dystocia, calving difficulty, is of great concern to the producer. It is estimated that 15% of bovine heifers will experience dystocia, requiring intervention to complete birthing process. In mature cows, about 3-5% of the population requires assistance, however, calves requiring an aided birth have a 50% heightened risk of mortality. Multiple factors contribute to this, among them hypoxia. Caffeine has been documented as an effective intervention to alleviate apnea episodes in human neonatal medicine. Caffeine is not considered a required nutrient of livestock and thus synthetic caffeine is not granted Generally Regarded As Safe (GRAS) consideration by The Association of American Feed Control Officials (AAFCO). However, naturally occurring forms of caffeine exist in tea leaves and tea is given GRAS status by AAFCO.

Many incidents of bovine dystocia result in hypoxic neonatal calves with profound edema of the head. This condition creates a state of drowsiness and recumbency thereby impairing calves' ability to stand and nurse colostrum which ultimately can be life threatening.

Human supplements containing synthetic caffeine can be administered to ameliorate the previously described deleterious effects of hypoxia. However, these commercially available products are not approved by AAFCO to be supplemented to livestock.

Weak calves are associated with being nutrient deprived. Anecdotally assumed to have low blood glucose, lethargic calves commonly receive supplemental quantities of glucose. Glucose supplementation incites an insulin response which decreases appetite and can result in periods of hypoglycemia which further amplifies lethargy, which is extremely detrimental in the first 12-24 hours of life when appetite is critical to colostrum intake, and colostrum intake is highly correlated to survivability and life-time productivity.

Thus, there remains a definite need for a bovine supplement for neonatal calves that does net contain synthetic caffeine, but provides needed energy, stimulates respiration and reduces edema.

SUMMARY OF THE INVENTION

By means of the present invention, there is provided a unique formulation for a bovine supplement for neonatal calves that delivers naturally occurring caffeine, antioxidants, and other electrolytes in a stable liquid form of moderate viscosity. The supplement successfully incorporates natural caffeine in a highly concentrated liquid oral dose formulation in which the viscosity of the liquid supplement is such that it facilitates adherence to the tongue and oral cavity, thereby facilitating mucosal absorption, which greatly enhances the effectiveness of the supplement. Additionally, due to the concentrated nature of the product caffeine can be delivered with minimal volume thereby minimizing satiety, resulting is ample capacity to intake sufficient quantities of colostrum. The viscosity is preferably in the range of 400 to 800 centipoise at 21 degrees Celsius and the specific gravity (relative density) is preferably in a range of 0.9-1.6.

The formula successfully adds naturally occurring caffeine in the form of green tea, which may be an extract, which is also rich in antioxidants and contains a high concentration of caffeine in a unique mix with xanthan gum, corn syrup, water and electrolytes. The corn syrup and xanthan gum are added to adjust the viscosity so that the solution sticks to the oral cavity and tongue to allow more rapid absorption of caffeine.

The supplement provides needed energy, stimulates respiration, reduces edema and stimulates muscle contraction.

DETAILED DESCRIPTION

The present invention provides a unique formulation for a neonatal bovine calf supplement to be administered following birth that delivers naturally occurring antioxidants, caffeine and electrolytes. The supplement successfully incorporates xanthan gum and a concentrated dose of caffeine which remains shelf stable in a liquid form and this has greatly enhanced the effectiveness of the supplement.

The present invention further has successfully added naturally occurring caffeine in the form of green tea in a liquid of moderate viscosity. The supplement not only provides needed energy, stimulates respiration, reduces edema, but it also stimulates muscle contraction. In this manner, the supplement treats the three biggest problems encountered by hypoxic calves—lethargy, respiratory rate, and high concentrations of adenosine. The supplement addresses potential survivability of calf through the effect of treatment.

One successful formula had the following range of ingredients.

| INGREDIENT | MIN % | MAX % |
| --- | --- | --- |
| Water | 25.00% | 55.00% |
| Green Tea | 1.00% | 15.00% |
| Sodium Citrate Dihydrate | 1.00% | 10.00% |
| Polysorbate 80 Liquid | 0.05% | 3.00% |
| Vegetable oil defoaming agent | 0.00% | 2.00% |
| Cassia Oil | 0.05% | 0.75% |
| Corn Syrup Blend | 40.00% | 75.00% |
| Citric Acid | 0.50% | 3.00% |
| Xanthan Gum | 0.05% | 5.00% |
| FD&C Blue Dye | ~.005% | ~.005% |

A successful product has about 2-3% green tea, 2-3% sodium citrate and less than 1% xanthan gum. A typical dose is 10-40 ml liquid solution and contains about 100-400 mg caffeine per dose. The supplement is a homogeneous solution when heated and packaged that becomes a suspension at room temperature. The solution is preferably bottled when warm. The supplement is shelf-stable and does not require a factory vacuum seal and it does not grow mold, yeast or bacteria. Cassia oil (cinnamon aldehyde), a flavor enhancer, also acts as a preservative.

This invention has been described herein in considerable detail in order to comply with the patent statutes and to provide those skilled in the art with the information needed to apply the novel principles and to construct and use embodiments of the example as required. However, it is to be understood that the invention can be carried out by specifically different devices and that various modifications can be accomplished without departing from the scope of the invention itself.

What is claimed is:

1. A neonatal bovine dietary supplement that delivers a dose of a naturally occurring source of caffeine to a neonatal calf, the supplement comprising non-synthetic caffeine in the form of green tea extract which is present in an amount of 1-15% wt, and a viscosity adjustor in liquid form, wherein a viscosity of the supplement is 400-800 centipoise at 21 degrees Celsius such that the supplement is absorbed through the oral mucosal lining of the neonatal calf.

2. The neonatal bovine dietary supplement of claim 1, wherein the viscosity adjustor comprises corn syrup and xanthan gum.

3. The neonatal bovine dietary supplement of claim 1 further comprising sodium citrate and vegetable oil defoaming agent for facilitating suspension of the green tea extract in the supplement.

4. The neonatal bovine dietary supplement of claim 3, wherein the sodium citrate is sodium citrate dihydrate.

5. The neonatal bovine dietary supplement of claim 1 further comprising an antioxidant.

6. The neonatal bovine dietary supplement of claim 1 further comprising electrolytes.

7. The neonatal bovine dietary supplement of claim 6, wherein the electrolytes comprise sodium citrate or sodium citrate dihydrate.

8. A neonatal bovine dietary supplement that delivers a dose of a naturally occurring source of caffeine to a neonatal calf, the supplement comprising non-synthetic caffeine in the form of green tea extract, and a viscosity adjustor in liquid form, wherein a viscosity of the supplement is 400-800 centipoise at 21 degrees Celsius such that the supplement is absorbed through the oral mucosal lining of the neonatal calf, wherein the green tea extract contains a concentrated amount of caffeine so that a 10-40 ml liquid dose of the supplement delivers 100-400 mg caffeine to the neonatal calf.

9. A neonatal bovine dietary supplement that delivers a dose of a naturally occurring source of caffeine to a neonatal calf, the supplement comprising green tea extract, xanthan gum, corn syrup, and water, wherein the corn syrup is present in the supplement in an amount of 40-75% wt, and wherein the viscosity of the supplement is 400-800 centipoise at 21 degrees Celsius such that the supplement is absorbed through the oral mucosal lining of the neonatal calf.

10. A neonatal bovine dietary supplement that delivers a dose of a naturally occurring source of caffeine to a neonatal calf, the supplement comprising green tea extract, xanthan gum, corn syrup, and water, wherein the green tea extract in the supplement is about 2-3% wt.

11. A method of use of a neonatal bovine dietary supplement containing a naturally occurring source of caffeine for a new-born calf, said method comprising:

(a) being presented with a new-born calf suffering from bovine dystocia;

(b) administering to the calf a dose of the supplement comprising non-synthetic caffeine and a viscosity adjustor in liquid form, wherein a viscosity of the supplement is 400-800 centipoise at 21 degrees Celsius; and (c) wherein the supplement is absorbed through the oral mucosal lining of the calf.

12. The method of claim 11, wherein the naturally occurring caffeine is provided by a green tea extract.

13. The method of claim 11, wherein the viscosity adjustor comprises corn syrup and xanthan gum.

14. The method of claim 12, wherein the supplement dose comprises 10-40 ml of liquid and the dose of the supplement delivers 100-400 mg caffeine to the neonatal calf.

\* \* \* \* \*